US010160960B2

(12) United States Patent
Landry et al.

(10) Patent No.: US 10,160,960 B2
(45) Date of Patent: Dec. 25, 2018

(54) MUTANTS OF COCAINE ESTERASE

(71) Applicants: The Trustees of Columbia University in the City of New York, New York, NY (US); University of Kentucky Research Foundation, Lexington, KY (US)

(72) Inventors: Donald Landry, New York, NY (US); Chang-Guo Zhan, Lexington, KY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/910,446

(22) PCT Filed: Aug. 6, 2014

(86) PCT No.: PCT/US2014/049990
§ 371 (c)(1),
(2) Date: Feb. 5, 2016

(87) PCT Pub. No.: WO2015/021187
PCT Pub. Date: Feb. 12, 2015

(65) Prior Publication Data
US 2016/0177277 A1    Jun. 23, 2016

Related U.S. Application Data

(60) Provisional application No. 61/862,955, filed on Aug. 6, 2013.

(51) Int. Cl.
*C12N 9/18*     (2006.01)
*A61K 38/46*   (2006.01)
*A61K 38/00*   (2006.01)

(52) U.S. Cl.
CPC ............ *C12N 9/18* (2013.01); *A61K 38/465* (2013.01); *C12Y 301/01084* (2013.01); *A61K 38/00* (2013.01)

(58) Field of Classification Search
None
See application file for complete search history.

(56) References Cited

U.S. PATENT DOCUMENTS

| 8,318,156 B2 | 11/2012 | Landry et al. | |
|---|---|---|---|
| 2010/0034799 A1* | 2/2010 | Landry | A61K 38/465 424/94.6 |
| 2011/0142816 A1 | 6/2011 | Landry et al. | |
| 2013/0039900 A1 | 2/2013 | Sunahara et al. | |

FOREIGN PATENT DOCUMENTS

| WO | WO2011081928 | 7/2001 | |
|---|---|---|---|
| WO | WO-2011081928 A2 * | 7/2011 | ............ A61K 38/465 |

OTHER PUBLICATIONS

Bresler et al., Gene cloning and nucleotide sequencing and properties of a cocaine esterase from *Rhodococcus*sp. Strain MB1, Applied and Environmental Microbiology, 2000, vol. 66, No. 3, pp. 904-908.
Collins et al., Repeated administration of a mutant cocaine esterase: effects on plasma cocaine levels, cocaine-induced cardiovascular activity, and immune responses in rhesus monkeys, The Journal of Pharmacology and Experimental Therapeutics, 2012, vol. 342, No. 1, pp. 205-213.
Cooper et al., Rapid and robust protection against cocaine-induced lethality in rats by the bacterial cocaine esterase, Molecular Pharmacology, 2006, vol. 70, No. 6, pp. 1885-1891.
Cryan, Carrier-based strategies for targeting protein and peptide drugs to the lungs, The AAPS Journal, 2004, vol. 7, No. 1, pp. E20-E41.
Dillon et al., RNAI as an experimental and therapeutic tool to study and regulate physiological and disease processes, Annual Review of Physiology, 2005, vol. 67, pp. 147-173.
Dykxhoorn et al., The silent revolution: RNA interference as basic biology, research tool, and therapeutic, Annual Review of Medicine, 2005, vol. 56, pp. 401-423. RNAi).
Elhai et al., Conjugal transfer of DNA to cyanobacteria, Methods in Enzymology, 1988, vol. 167, pp. 747-754.
Fanning et al., Gene-expressed RNA as a therapeutic: issues to consider, using ribozymes and small hairpin RNA as specific examples, Handb Exp. Pharmacol, 2006, vol. 173, pp. 289-303.
Fee et al., PEG-proteins: Reaction engineering and separation issues, Chemical Engineering Science, 2006, vol. 62, No. 3, pp. 924-939.
Fee, Protein conjugates purification and characterization, PEGylated Protein Drugs: Basic Science and Clinical Application, 2003, pp. 113-125.
Fee, Size-exclusion reaction chromatography (SERC): A new technique for protein PEGylation, Biotechnology and Bioengineering, 2003, vol. 82, No. 2, pp. 200-206.
Galovic et al., High efficiency entrapment of superoxide dismutase into mucoadhesive chitosan-coated liposomes, European Journal of Pharmaceutical Sciences, 2002, vol. 15, No. 5, pp. 441-448.
Gao et al., Thermostable Variants of cocaine esterase for long-time protection against cocaine toxicity, Molecular Pharmacology, 2009, vol. 75, No. 2, pp. 318-323.
Ghadessy et al., Directed evolution of polymerase function by compartmentalized self-replication, Proceedings of the National Academy of Sciences of the United States of America, 2001, vol. 98, No. 8, pp. 4552-4557.
Helene et al., Control of gene expression by triple helix-forming oligonucleotides. The Antigene strategy, Annals of the New York Academy of Sciences, 1992, vol. 660, pp. 27-36.
International Search Report and Written Opinion dated Dec. 17, 2014 in related International Application No. PCT/US14/49990 filed Aug. 6, 2014, 8 pages.
Jonkman et al., Molecular, cellular, and structural mechanisms of cocaine addiction: a key role for microRNAs, Neuropsychopharmacology, 2013, vol. 38, No. 1, pp. 198-211.

(Continued)

*Primary Examiner* — Emily A Cordas
(74) *Attorney, Agent, or Firm* — Dentons US LLP

(57) ABSTRACT

Provided are mutant cocaine esterase polypeptides and PEGylated formulations thereof.

23 Claims, 9 Drawing Sheets

Specification includes a Sequence Listing.

(56) References Cited

OTHER PUBLICATIONS

Lee et al., Aptamer Therapeutics advance, Current Opinion in Chemical Biology, 2006, vol. 10, No. 3, pp. 282-289.
Link et al., Beyond Toothpicks: new methods for isolating mutant bacteria, Nature Reviews, 2007, vol. 5, No. 9, pp. 680-688.
Maher, DNA triple-helix formation: an approach to artificial gene repressors, BioEssays, 1992, vol. 14, No. 12, pp. 807-815.
Narasimhan et al., Structural analysis of thermostabilizing mutations of cocaine esterase, Protein Eng Des Sel., 2010, vol. 23, No. 7, pp. 537-547.
Pushparaj et al., Short intefering RNA (siRNA) as a novel therapeutic, Clinical and Experimental Pharmacology and Physiology, 2006, vol. 33, No. 5-6, pp. 504-510.
Reynolds et al., Rational siRNA design for RNA interference, Nature Biotechnology, 2004, vol. 22, No. 3, pp. 326-330.
Sagner et al., Rapid filter assay for the detectino of DNA polymerase activity: direct identification of the gene for the DNA polymerase from *Thermus aquaticus*, Gene, 1991, vol. 97, No. 1, pp. 119-123.
Sakiyama et al., Development of growth factor fusion proteins for cell-triggered drug delivery, FASEB J., 2001, vol. 15, No. 7, pp. 1300-1302.
Stayton et al., "Smart" delivery systems for biomolecular therapeutics, Orthod Craniofacial Res 8, 2005, pp. 219-225.
Studier, Protein production by auto-induction in high-density shaking cultures, Protein Expression and Purification, 2005, vol. 41, No. 1, pp. 207-234.
Teng et al., Functional recovery following traumatic spinal cord injury mediated by a unique polymer scaffold seeded with neural stem cells, Proceedings of the National Academy of Sciences of the United States of America, 2002, vol. 99, No. 5, pp. 3024-3029.
Varde et al., Microspheres for controlled release drug delivery, Expert Opinion on Biological Therapy, 2004, vol. 4, No. 1, pp. 35-51.
Wagner et al., The crossflow injection technique: an improvement of the ethanol injection method, Journal of Liposome Research, 2002, vol. 12, No. 3, pp. 259-270.
Wu et al., Arming antibodies: prospects and challenges for immunoconjugates, Nature Biotechnology, 2005, vol. 23, No. 9, pp. 1137-1146.
Zheng et al., Modeling of pharmacokinetics of cocaine in human reveals the feasibility for development of enzyme therapies for drugs of abuse, PLOS Computational Biology, 2012, vol. 8, No. 7, 10 pages.

\* cited by examiner

SEQUENCE LISTING

<160> NUMBER OF SEQ ID NOS: 1

<210> SEQ ID NO 1
<211> LENGTH: 574
<212> TYPE: PRT
<213> ORGANISM: Rhodococcus sp. strain MB1

<400> SEQUENCE: 1

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
        130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365
```

-continued

```
Ala Asn Thr Ser Thr Gly Gly Gly Thr Leu Ser Thr Ser Ile Ser Gly
    370             375             380

Thr Glu Ser Ala Asp Thr Tyr Leu Tyr Asp Pro Ala Asp Pro Val Pro
385             390             395             400

Ser Leu Gly Gly Thr Leu Leu Phe His Asn Gly Asp Asn Gly Pro Ala
            405             410             415

Asp Gln Arg Pro Ile His Asp Arg Asp Asp Val Leu Cys Tyr Ser Thr
            420             425             430

Glu Val Leu Thr Asp Pro Val Glu Val Thr Gly Thr Val Ser Ala Arg
        435             440             445

Leu Phe Val Ser Ser Ala Val Asp Thr Asp Phe Thr Ala Lys Leu
    450             455             460

Val Asp Val Phe Pro Asp Gly Arg Ala Ile Ala Leu Cys Asp Gly Ile
465             470             475             480

Val Arg Met Arg Tyr Arg Glu Thr Leu Val Asn Pro Thr Leu Ile Glu
            485             490             495

Ala Gly Glu Ile Tyr Glu Val Ala Ile Asp Met Leu Ala Thr Ser Asn
            500             505             510

Val Phe Leu Pro Gly His Arg Ile Met Val Gln Val Ser Ser Ser Asn
        515             520             525

Phe Pro Lys Tyr Asp Arg Asn Ser Asn Thr Gly Gly Val Ile Ala Arg
    530             535             540

Glu Gln Leu Glu Glu Met Cys Thr Ala Val Asn Arg Ile His Arg Gly
545             550             555             560

Pro Glu His Pro Ser His Ile Val Leu Pro Ile Ile Lys Arg
            565             570
```

MUTANTS OF COCAINE ESTERASE

CROSS REFERENCE TO RELATED APPLICATIONS

The present application claims the benefit of priority to PCT International Application No. PCT/US14/49990 filed 6 Aug. 2014, which claims the benefit of U.S. Provisional Application Ser. No. 61/862,955 filed 6 Aug. 2013; each of which is incorporated herein by reference in its entirety.

STATEMENT REGARDING FEDERALLY SPONSORED RESEARCH OR DEVELOPMENT

Not Applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

BACKGROUND OF THE INVENTION

Cocaine is a highly addictive substance of abuse and its use maintains the drug-taking habit by directly affecting the reward pathways. Cocaine use can have detrimental physical and emotional consequences. Regardless of the frequency of use cocaine users can experience heart attacks or strokes. Cocaine abusers can also subject to experiencing anxiety, depression, or paranoia. Currently there are no small molecule drugs that can block the addictive or toxic effects of cocaine. However, it has been shown that an enzyme called cocaine esterase (CocE) can accelerate the breakdown of circulating cocaine or reduce its effects. Bacterial CocE has been found to be easily expressed or purified ($K_{cat}$=7.8 s$^{-1}$ $K_m$=<1 µM). Administration of a cocaine esterase (CocE) can decrease the half-life of cocaine in both the brain or plasma. A major hurdle with using CocE as a therapeutic is that it can be unstable and can be quickly degraded.

A strategy to antagonize the negative effects of cocaine has been to increase its metabolism by using cocaine-specific enzymes, such as cocaine esterase (CocE). The use of cocaine specific enzymes have shown to decrease the half-life of cocaine in both the plasma and in the brain. But a limitation is that CocE can be unstable in vivo and can have a very low half-life.

SUMMARY OF THE INVENTION

Among the various aspects of the present disclosure is the provision of a composition including an isolated mutant cocaine esterase (CocE) polypeptide. In some embodiments, the CocE polypeptide of the composition has an amino acid sequence having at least about 95% sequence identity to SEQ ID NO: 1 and one or more substitution, addition or deletion selected from the group consisting of C107S, C429S, C551S, A328C, D18C, T436C, V434C, L163V; V121D; S167A, W52L, Q123E, S159A, T122A, S140A, T172R, G173Q, S265A, W220A, A193D, and Y532F, wherein the polypeptide has cocaine esterase activity.

In some embodiments, the composition further includes a polymeric molecule chemically linked to the mutant CocE polypeptide. In some embodiments, the composition further includes a plurality of polymeric molecules chemically linked to the mutant CocE polypeptide. In some embodiments, the composition further includes a plurality of polymeric molecules coating the mutant CocE polypeptide.

Another aspect provides a nucleic acid molecule encoding the mutant CocE polypeptide.

Another aspect provides a method of treating a cocaine-induced condition via administering an effective amount of a composition as described above and herein to a subject in need thereof.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 3 is a series of line and scatter plots and data depicting the functional kinetic changes resulting from a structural change from substitution of cysteine in CocE.

DETAILED DESCRIPTION OF THE INVENTION

Figure 1:
FIG. 1 is a PYMOL-generated 3D configuration of CocE polypeptide with locations of cysteine mutations labeled.
Figure 2:
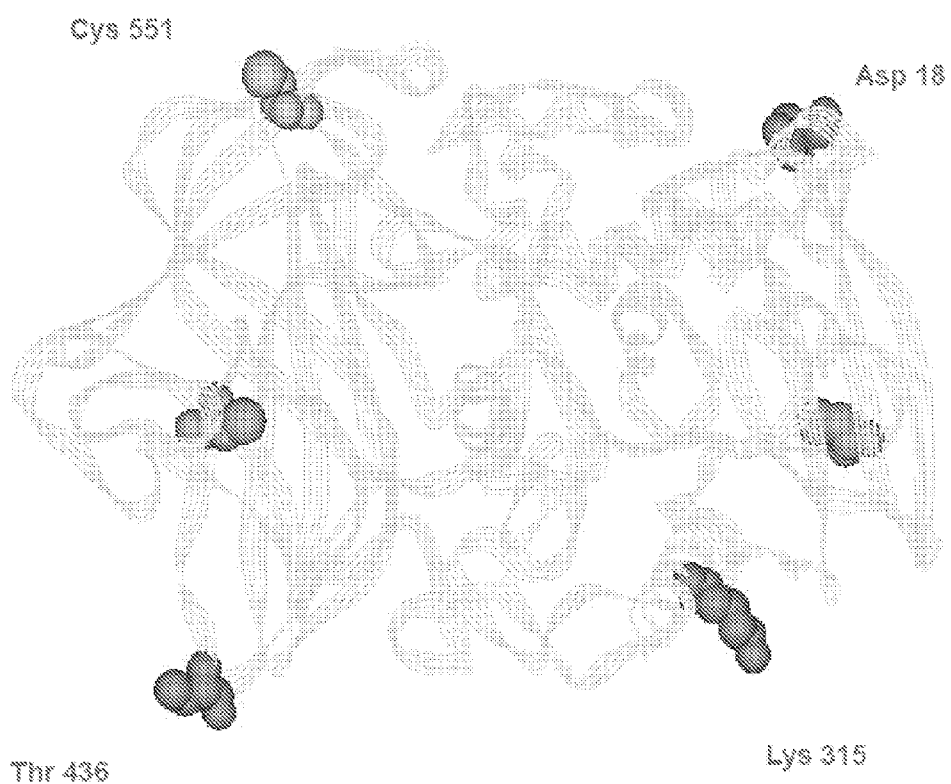
FIG. 2 is a structural model of CocE with Cys 551, Asp 18, Lys 315, and Thr 436 positions labeled.
Figure 3A:
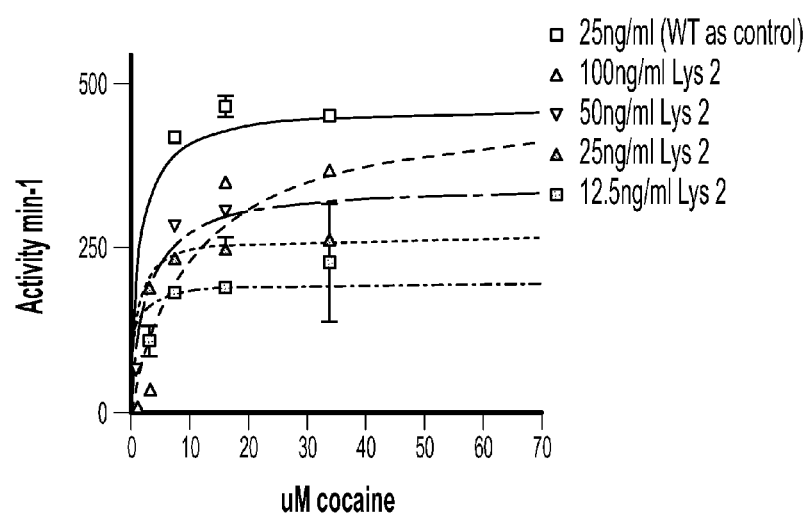
FIG. 3A is a line and scatter plot of the Lys2: C107S, C429S CocE mutation and corresponding Activity data.
Figure 3B:
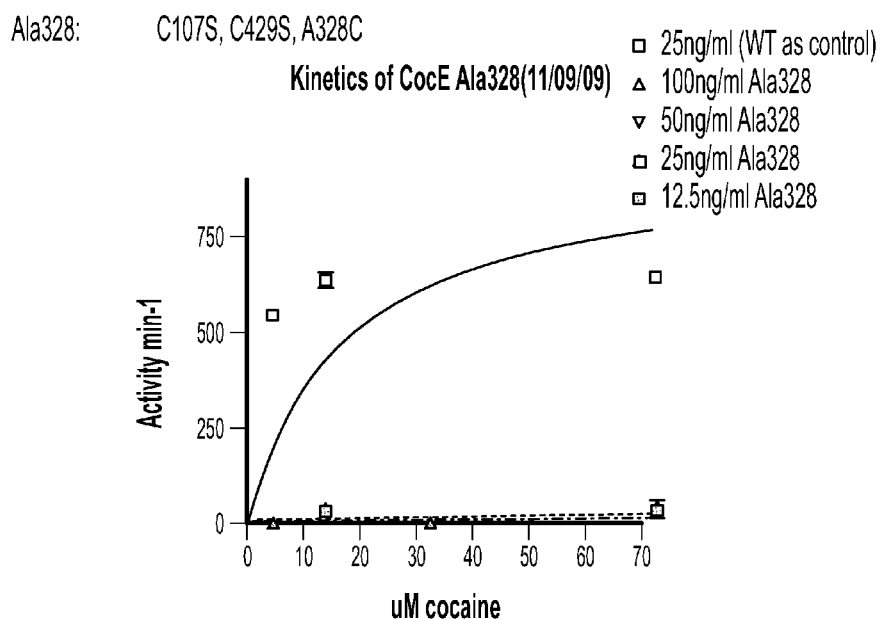
FIG. 3B is a line and scatter plot of the A1a328: C107S, C429S, A328C CocE mutation and corresponding activity data.
Figure 3C:
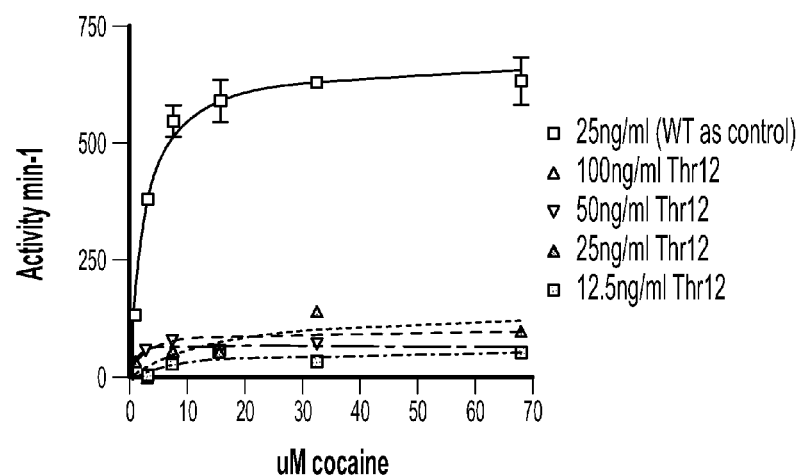
FIG. 3C is a line and scatter plot of the Thr12: C107S, C429S, T436C CocE mutation and corresponding activity data.
Figure 3D:
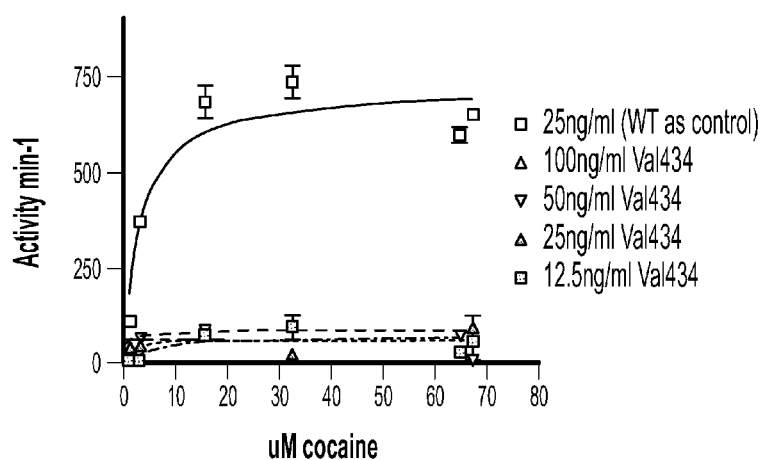
FIG. 3D is a line and scatter plot of the Val434: C107S, C429S, V434C CocE mutation and corresponding activity data.

The present disclosure is based, at least in part, on the discovery that mutations made to CocE can increase stability or enzymatic efficiency. As shown herein, mutations of CocE and optional linkage to a polymeric molecule can enhance the pharmaceutical properties of cocaine esterase (CocE) by shielding of antigenic or immunogenic epitopes, preventing degradation by proteolytic enzymes, increasing water-solubility, reducing the renal filtration, or altering biodistribution. Approaches identified can include linkage of a CocE and a polymeric molecule, such as site-directed coating of the protein, e.g., through PEGylation. Attaching a hydrophilic polymer can make the proteins less immunogenic (e.g., as shown in asparaginase and adenosine-deaminase) and provide other benefits described more fully below.

A sulfhydryl group of a cysteine amino acid residue on the surface of a protein can be an ideal site for attachment of a polymeric molecule. Site directed mutagenesis can allow substitution of a cysteine for any amino acid in the primary sequence of CoCE. The placement of a plurality of cysteines for use as attachment sites for large polymeric molecules can require that they be distributed over the surface of CoCE. If not distributed, then reaction at one cysteine may block reaction at an adjacent cysteine. Because an initial reaction can occur randomly at two sites, the result can be a mixture. If there are several cysteines that are poorly distributed, the result can be a complex mixture. Such mixtures may be undesirable because the activity and stability of a mutant CoCE may not be attributed to a single chemical entity and thus may not be optimized effectively. Not only can cysteines introduced into CoCE react but native cysteines can also couple with activated polymeric molecules and if not effectively distributed, the result can be an undesirable complex mixture. But native cysteines can contribute to the stability and efficiency of enzymes, and their removal may not be tolerated in some embodiments. In some embodiments, determination of whether a particular amino acid can be substituted for a native cysteine is determined through experimentation.

As shown herein, various mutations were made and identified in CocE that remove poorly distributed native cysteines without unacceptable loss of stability and enzymatic efficiency. Mutant variants of CocE and coated CocE mutants disclosed herein can be designed to have an amino acid structure unencumbered by poorly distributed surface cysteines. Accordingly, various CocE mutants can be used for developing mutants with added cysteines so as to develop coated CoCE mutants for use as an effective enzyme therapy for cocaine intoxication and addiction in humans.

In various embodiments, one or more specific mutations of cysteine (C) (e.g., to serine (S)) can be made to CocE. As stated, poorly distributed native cysteine residues can be a major contributing factor for complex mixtures of polymeric coated CocE. Exemplary mutations include: C107; C429; C551; or C477. While in no way limiting the present disclosure, it is presently thought that C107, C429, or C551 are exposed to solvent and could be maldistributed relative to the ideal substitution of surface cysteines for attachment of polymeric molecules. While in no way limiting the present disclosure, it is presently thought that C477 may be a conserved structural component. Activity assays of other CocE constructs which contain mutations including C107S or C429S mutations determined the Michaelis constant (Km) and maximal reaction velocity (Vmax) of the mutants compared to wild-type control.

CocE mutants, as described herein, can be used to protect against the toxic effect of cocaine, treat and prevent cocaine addiction, reduce the plasma levels of cocaine in an overdose emergency, or improve the efficacy of long-lasting cocaine esterase as a biologic therapeutic.

MUTANT CocE POLYPEPTIDES

Described herein are CocE mutant polypeptides. A mutant CocE polypeptide can have an amino acid sequence of a CocE polypeptide (e.g., a wild-type CocE) with one or more mutations (e.g., substitution, addition, or deletion). For example, a mutant CocE polypeptide can have an amino acid sequence of wild type CocE from *Rhodococcus* sp. (SEQ ID NO: 1) with at least one or more mutations (e.g., substitution, addition, or deletion). As another example, a mutant CocE polypeptide can have at least about 80% sequence identity to SEQ ID NO: 1 (e.g., at least about 85%, at least about 90%, at least about 95%, at least about 96%, at least about 97%, at least about 98%, or at least about 99%) and having at least one or more mutations described herein and substantially retaining CocE activity or increased stability.

In some embodiments, a mutation of a CocE polypeptide can provide for increased stability by removing or replacing an amino acid residue associated with instability. For example, a mutation of a CocE can replace or eliminate a cysteine residue (e.g., C107, C429, C551, or C477 from SEQ ID NO: 1). A cysteine residue of a CocE polypeptide can be replaced by one or more amino acids such that CocE activity is retained or stability is increased. For example, one of more cysteine resides of CocE can be replaced with a serine residue (e.g., C107S, C429S, C551 S, or C477S from SEQ ID NO: 1). The above listed mutations can be in combination with (e.g., in addition to) other mutations described herein.

In some embodiments, one or more native cysteine residues of CoCe can be substituted so as to remove ineffective distribution of cysteines that can result in undesirable complex mixture. In various embodiments, an additional one or more cysteines can be introduced so as to provide an optimized distribution (e.g., a geometrically optimized distribution) of cysteines to form an effective anchor point for attachment of one or more polymer molecules to CocE. For example, C107 and C429 can be removed and an additional one or more cysteines can be substituted (e.g., K315C; T436C; N19Cs; V434C; or A328C).

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations described herein and retaining cocaine esterase activity. For example, a mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations at positions C107, C429, C551, or C477 (e.g., C107S, C429S, C551S, or C477S). In some embodiments, mutations at positions C107, C429, C551, or C477 are not C107A, C429A, C551A, or C477A, respectively (see e.g., Example 5, Table 1).

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of A328C, D18C, T436C, V434C, L163V; V121D; S167A, W52L, Q123E, S159A, T122A, S140A, T172R, S265A, W220A, A193D, or Y532F (including but not limited to combinations with mutations at positions C107, C429, C551, or C477). A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of C107S, C429S, C551 S, C477S, A328C, D18C, T436C, V434C, L163V; V121D; S167A, W52L, Q123E, S159A, T122A, S140A, T172R, S265A, W220A, A193D, or Y532F. The above listed mutations can be in combination with (e.g., in addition to) other mutations described herein.

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of: C107S and C429S; C107S, C429S, and A328C; D18C, C107S, and C429S; C107S, C429S, T436C; or C107S, C429S, and V434C. The above listed mutations can be in combination with (e.g., in addition to) other mutations described herein.

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of R41I, N42V, Y44F, D45R, F47R, K46A, S56G, T74S, F84Y, S117A, L119A, G173Q, S140A, L146P, A149S, Y152H, S159A, V160A, L163V, L169K, G171A, T172R, G173A, G173Q, L174R, S177Q, A181K, S179R, R182K, F189A, F189K, F189L, V190K, Q191K, A193D, A194K, A194R, N197K, I218L, W220A, V225I, T254R, V262L, S265A, W285T, A310D, C477T, L508G, K531A, Y532F, D533S, T172R/G173Q, T172R/A193D, T172R/F189K, T172R/G173Q-I175-G-G-A186, G171Q/T172R/G173Q, T172R/G173Q-T176-G-G-D185, G173Q-I175-G-G-A186, G173Q-T176-G-G-D185, I175-G-G-A186, T176-G-G-D185, wt-I175-G-D185, wt-T176-G-G-D185, and F189A/T172R. In some embodiments, a mutant CocE polypeptide has at least a G173Q mutation. The above listed mutations can be in combination with (e.g., in addition to) other mutations described herein.

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of R75K, F78C, F78R, A79K, A79R, Y118S, V121Y, L164K, W166R, I170V, G173Q, T176R, S177C, K315C, G171S, D180K, P183K, F78C/S177C, or Y118S/V121Y. In some embodiments, a mutant CocE polypeptide has at least a G173Q mutation. The above listed mutations can be in combination with (e.g., in addition to) other mutations described herein.

A mutant CocE polypeptide can have an amino acid sequence according to SEQ ID NO: 1, or a variant thereof having at least about 80% sequence identity (e.g., at least about 85%, at least about 90%, at least about 95%, at least about 96%, at least about 97%, at least about 98%, or at least about 99%), with one or more mutations of C107S, C429S, C551S, C477S, A328C, D18C, T436C, V434C, L163V, V121D, S167A, W52L, Q123E, S159A, T122A, S140A, T172R, S265A, W220A, A193D, Y532F, R41I, N42V, Y44F, D45R, F47R, K46A, S56G, T74S, F84Y, S117A, L119A, G173Q, S140A, L146P, A149S, Y152H, S159A, V160A, L163V, L169K, G171A, T172R, G173A, G173Q, L174R, S177Q, A181K, S179R, R182K, F189A, F189K, F189L, V190K, Q191K, A193D, A194K, A194R, N197K, I218L, W220A, V225I, T254R, V262L, S265A, W285T, A310D, C477T, L508G, K531A, Y532F, D533S, T172R/G173Q, T172R/A193D, T172R/F189K, T172R/G173Q-I175-G-G-A186, G171Q/T172R/G173Q, T172R/G173Q-T176-G-G-D185, G173Q-I175-G-G-A186, G173Q-T176-G-G-D185, I175-G-G-A186, T176-G-G-D185, wt-I175-G-D185, wt-T176-G-G-D185, F189A/T172R, R75K, F78C, F78R, A79K, A79R, Y118S, V121Y, L164K, W166R, I170V, G173Q, T176R, S177C, K315C, G171S, D180K, P183K, F78C/S177C, or Y118S/V121Y. In some embodiments, a mutant CocE polypeptide has at least a G173Q mutation. The above listed mutations can be in combination with (e.g., in addition to) other mutations described herein.

CocE mutations, which are suitable for uses and methods according to the present invention are disclosed in U.S. Pat. No. 8,318,156, issued 27 Nov. 2012, which is incorporated herein in its entirety with regard to the generation of mutant CocE polypeptides, transformation, purification, assays and methods of use of the mutant CocE polypeptides.

CocE mutations, which are suitable for uses and methods according to the present invention are disclosed in US Pat Pub No. 2013/0039900, published 14 Feb. 2013.

Polymer

A mutant CocE polypeptide can be linked to a polymeric molecule. A polymer molecule for linking to a CocE polypeptide can be non-toxic, non-immunogenic, non-antigenic, highly soluble in water, or FDA approved. A mutant CocE polypeptide can comprise a polymeric coating.

A polymeric molecule for linkage or coating a mutant CocE polypeptide can have a molecular weight suitable to achieve benefits described herein without sacrificing CocE activity or incurring other negative effects. For example, a polymeric molecule for linkage or coating a mutant CocE polypeptide can have a molecular weight of about 300 Daltons up to about 20,000 Daltons. As another example, a polymeric molecule for linkage or coating a mutant CocE polypeptide can have a molecular weight of about 500 Daltons, about 750 Daltons, about 1000 Daltons, about 1500 Daltons, about 2000 Daltons, about 2500 Daltons, about 3000 Daltons, about 3500 Daltons, about 4000 Daltons, about 4500 Daltons, about 5000 Daltons, about 5500 Daltons, about 6000 Daltons, about 6500 Daltons, about 7000 Daltons, about 7500 Daltons, about 8000 Daltons, about 8500 Daltons, about 9000 Daltons, about 9500 Daltons, about 10000 Daltons, about 10500 Daltons, about 11000 Daltons, about 11500 Daltons, about 12000 Daltons, about 12500 Daltons, about 13000 Daltons, about 13500 Daltons, about 14000 Daltons, about 14500 Daltons, about 15000 Daltons, about 15500 Daltons, about 16000 Daltons, about 16500 Daltons, about 17000 Daltons, about 175000 Daltons, about 18000 Daltons, about 18500 Daltons, about 19000 Daltons, about 19500 Daltons, or about 20000 Daltons. It is understood that the ranges between each of the above listed molecular weights are included in the present disclosure. It is understood that the above described molecular weights and ranges thereof apply generically to polymeric molecules and specifically to polymeric molecules such as polyethylene glycol, described more fully below.

In some embodiments, a polymeric molecule for linking to a mutant CocE polypeptide comprises: 2-[2-(Boc-amino)ethoxy]ethoxyacetic acid (dicyclohexylammonium); 21-(Boc-amino)-4,7,10,13,16,19-hexaoxaheneicosanoic acid purum; 15-(Boc-amino)-4,7,10,13-tetraoxapentadecanoic acid purum; N-Boc-2,2'-(ethylenedioxy)diethylamine; N-Boc-N'-succinyl-4,7,10-trioxa-1,13-tridecanediamine; 2-[2-(Fmoc-amino)ethoxy]ethanol; N-Fmoc-N"-succinyl-4,7,10-trioxa-1,13-tridecanediamine; 4,7,10,13,16,19,22,25,32,35,38,41,44,47,50,53-Hexadecaoxa-28,29-dithiahexapentacontanedioic acid; 4,7,10,13,16,19,22,25,32,35,38,41,44,47,50,53-Hexadecaoxa-28,29-dithiahexapentacontanedioic acid di-N-succinimidyl ester; O,O'-Bis(2-aminoethyl)octadecaethylene glycol; {2-[2-(Fmoc-amino)ethoxy]ethoxy}acetic acid; 2-[2-(2-Methoxyethoxy)ethoxy]acetic acid; methoxypolyethylene glycol maleimide; O-(2-Azidoethyl)-O'-methyl-triethylene glycol; O-(2-Azidoethyl)-O'-methyl-undecaethylene glycol; O-(2-Azidoethyl)nonadecaethylene glycol; O,O'-Bis[2-(N-Succinimidyl-succinylamino)ethyl]polyethylene glycol; O,O'-Bis[2-(N-Succinimidyl-succinylamino)ethyl]polyethylene glycol; O-(3-Carboxypropyl)-O'-[2-(3-mercaptopropionylamino)ethyl]-polyethylene glycol; O—[N-(3-Maleimidopropionyl)aminoethyl]-O'-[3-(N-succinimidyloxy)-3-oxopropyl]triethylene glycol; Methoxypolyethylene glycol azide PEG; Methoxypolyethylene glycol maleimide; or O-[2-(3-Tritylthiopropionylamino)ethyl]polyethylene glycol.

In some embodiments, a mutant CocE polypeptide is linked to a polyethylene glycol (PEG) polymer (i.e., PEGylated). A PEG linked to a mutant CocE polypeptide can have a molecular weight as described above. For example, a PEG for linkage or coating a mutant CocE polypeptide can have a molecular weight of about 500 Daltons up to about 20,000 Daltons (or any of the molecular weights or ranges described above).

PEGylation is understood as the process of covalent attachment of polyethylene glycol (PEG) polymer chains to another molecule, such as a drug or therapeutic protein. The structure of PEG is understood as $H-(O-CH_2-CH_2)_n-OH$, where the parentheses contain the repeated element. A PEG can be polyethylene oxide (PEO) or polyoxyethylene (POE). PEG can have a molecular weight from about 300 g/mol to about 10,000,000 g/mol.

In some embodiments, a different form of PEG is used, according to the initiator used for the polymerization process. For example, a monofunctional methyl ether PEG, or methoxypoly(ethylene glycol) (mPEG) can be used.

PEGylation can be achieved by incubation of a reactive derivative of PEG with the target molecule, e.g., a mutant CocE described herein. Covalent attachment of PEG to a mutant CocE polypeptide can "mask" the polypeptide from a host's immune system (e.g., providing reduced immunogenicity or antigenicity), or increase the hydrodynamic size (size in solution) of the mutant CocE polypeptide which can prolong its circulatory time (e.g., by reducing renal clearance). PEGylation can also provide increased water solubility.

PEGylation can alter physiochemical properties of a mutant CocE polypeptide including changes in conformation, electrostatic binding, hydrophobicity, etc. These and other physical and chemical changes can increase systemic retention of the mutant CocE polypeptide. Also, PEGylation may influence the binding affinity of a mutant CocE polypeptide to cell receptors and may alter the absorption and distribution patterns.

PEGylation, by increasing the molecular weight of a molecule, such as a mutant CocE polypeptide, can impart significant pharmacological advantages over the unmodified form, including but not limited to: improved solubility; reduced dosage frequency, without diminished efficacy with potentially reduced toxicity; extended circulating life; increased drug stability; or enhanced protection from proteolytic degradation. A PEGylated mutant CocE polypeptide can have: increased water solubility; higher mobility in solution; lower toxicity; lower immunogenicity; ready clearance from the body; or altered distribution in the body.

PEGylation can include suitable functionalization of a PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer can be prepared to attach the PEG to a mutant CocE polypeptide.

PEGylation can be according to a solution phase batch process or an on-column fed-batch process (see generally, Fee et al. 2006 Chemical Engineering Science 61(3), 924). For example, a batch process can involve mixing of reagents together in a suitable buffer solution, e.g., at a temperature between 4 and 6° C., followed by the separation and purification of the desired product using a suitable technique based on its physicochemical properties, including size exclusion chromatography (SEC), ion exchange chromatography (IEX), hydrophobic interaction chromatography (HIC) and membranes or aqueous two phase systems (see generally, Fee 2003 "Protein conjugates purification and characterization", PEGylated Protein Drugs: Basic Science and Clinical Applications, Veronese, Ed. Birkhauser Publishing: Basel, 113-125; Fee 2003 Biotechnology and Bioengineering 82(2), 200-206).

Polymer linkage to a mutant CocE polypeptide can be according to any method recognized in the art. For example, PEG can be conjugated to a primary amine or thiol. An amino group (e.g. lysine) of a mutant CocE polypeptide can be conjugated to PEG by, e.g., alkylation or acylation. Alkylation can maintain a positively charged amine, whereas acylation can yield a neutral amide linkage. Acylation can occur via an N-hydroxysuccinimide (NHS) activated carboxylated PEG. An azide functionalized PEG can allow Staudinger ligation or Huisgen dipolar cycloaddition techniques. The introduction of a different protecting group can be useful for macromolecular cross-linking agents and spacers. Mutant CocE polypeptide target moieties can be specifically addressed with an appropriate functionalized PEG linker.

A choice of suitable functional group for the PEG derivative can based on the type of available reactive group on the mutant CocE polypeptide that will be coupled to the PEG. For a mutant CocE polypeptide, reactive amino acids can include, for example, lysine, cysteine, histidine, arginine, aspartic acid, glutamic acid, serine, threonine, or tyrosine. The N-terminal amino group and the C-terminal carboxylic acid can also be used as a site specific site by conjugation with aldehyde functional polymers. In some embodiments, a PEGylation can occur at a mutated position of the CocE polypeptide. For example, PEGylation can occur at one or more of mutations at C107, C429, C551, or C477 from SEQ ID NO: 1. As another example, PEGylation can occur at one or more of mutations at C107S, C429S, C551S, or C477S from SEQ ID NO: 1.

A first generation PEG derivative can be formed by reacting a PEG polymer with a group that is reactive with hydroxyl groups, e.g., anhydrides, acid chlorides, chloroformates or carbonates. In the second generation PEGylation chemistry more efficient functional groups such as aldehyde, esters, amides etc. can be made available for conjugation.

Heterobifunctional PEGs can be useful in linking two entities (e.g., a mutant CocE polypeptide and another entity, or two mutant CocE polypeptides), where a hydrophilic, flexible and biocompatible spacer is needed. Exemplary end groups for heterobifunctional PEGs are maleimide, vinyl sulfones, pyridyl disulfide, amine, carboxylic acids and NHS esters.

In some embodiments, PEGylation of a CocE polypeptide involves a homobifunctionalized, heterobifunctionalized, or mono-methoxy endcapped PEG.

The shape of the PEG polymer can be branched, star shaped, Y shaped or comb shaped, where such shapes can reduce viscosity or lack of organ accumulation. Branched PEGs can have about three to about ten PEG chains emanating from a central core group. Star PEGs can have about 10 to about 100 PEG chains emanating from a central core group. Comb PEGs can have multiple PEG chains normally grafted onto a polymer backbone.

Molecular Engineering

The following definitions and methods are provided to better define the present invention and to guide those of ordinary skill in the art in the practice of the present invention. Unless otherwise noted, terms are to be understood according to conventional usage by those of ordinary skill in the relevant art.

Molecular engineering can be as described in U.S. Pat. No. 8,318,156, issued 27 Nov. 2012, and incorporated herein by reference in its entirety.

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

Expression vector, expression construct, plasmid, or recombinant DNA construct is generally understood to refer to a nucleic acid that has been generated via human intervention, including by recombinant means or direct chemical synthesis, with a series of specified nucleic acid elements that permit transcription or translation of a particular nucleic acid in, for example, a host cell. The expression vector can be part of a plasmid, virus, or nucleic acid fragment. Typically, the expression vector can include a nucleic acid to be transcribed operably linked to a promoter.

A "promoter" is generally understood as a nucleic acid control sequence that directs transcription of a nucleic acid. An inducible promoter is generally understood as a promoter that mediates transcription of an operably linked gene in response to a particular stimulus. A promoter can include necessary nucleic acid sequences near the start site of transcription, such as, in the case of a polymerase II type promoter, a TATA element. A promoter can optionally include distal enhancer or repressor elements, which can be located as much as several thousand base pairs from the start site of transcription.

A "transcribable nucleic acid molecule" as used herein refers to any nucleic acid molecule capable of being transcribed into a RNA molecule. Methods are known for introducing constructs into a cell in such a manner that the transcribable nucleic acid molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present disclosure, conventional compositions and methods for preparing and using constructs and host cells are well known to one skilled in the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754).

The "transcription start site" or "initiation site" is the position surrounding the first nucleotide that is part of the transcribed sequence, which is also defined as position +1. With respect to this site all other sequences of the gene and its controlling regions can be numbered. Downstream sequences (i.e., further protein encoding sequences in the 3' direction) can be denominated positive, while upstream sequences (mostly of the controlling regions in the 5' direction) are denominated negative.

"Operably-linked" or "functionally linked" refers preferably to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation. The two nucleic acid molecules may be part of a single contiguous nucleic acid molecule and may be adjacent. For example, a promoter is operably linked to a gene of interest if the promoter regulates or mediates transcription of the gene of interest in a cell.

A "construct" is generally understood as any recombinant nucleic acid molecule such as a plasmid, cosmid, virus, autonomously replicating nucleic acid molecule, phage, or linear or circular single-stranded or double-stranded DNA or RNA nucleic acid molecule, derived from any source, capable of genomic integration or autonomous replication, comprising a nucleic acid molecule where one or more nucleic acid molecule has been operably linked.

A constructs of the present disclosure can contain a promoter operably linked to a transcribable nucleic acid molecule operably linked to a 3' transcription termination nucleic acid molecule. In addition, constructs can include but are not limited to additional regulatory nucleic acid molecules from, e.g., the 3'-untranslated region (3' UTR). Constructs can include but are not limited to the 5' untranslated regions (5' UTR) of an mRNA nucleic acid molecule which can play an important role in translation initiation and can also be a genetic component in an expression construct. These additional upstream and downstream regulatory nucleic acid molecules may be derived from a source that is native or heterologous with respect to the other elements present on the promoter construct.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism such as a bacterium, cyanobacterium, animal or a plant into which a heterologous nucleic acid molecule has been introduced. The nucleic acid molecule can be stably integrated into the genome as generally known in the art and disclosed (Sambrook 1989; Innis 1995; Gelfand 1995; Innis & Gelfand 1999). Known methods of PCR include, but are not limited to, methods using paired primers, nested primers, single specific primers, degenerate primers, gene-specific primers, vector-specific primers, partially mismatched primers, and the like. The term "untransformed" refers to normal cells that have not been through the transformation process.

"Wild-type" refers to a virus or organism found in nature without any known mutation.

Design, generation, and testing of the variant nucleotides, and their encoded polypeptides, having the above required percent identities and retaining a required activity of the expressed protein is within the skill of the art. For example, directed evolution and rapid isolation of mutants can be according to methods described in references including, but not limited to, Link et al. (2007) Nature Reviews 5(9), 680-688; Sanger et al. (1991) Gene 97(1), 119-123; Ghadessy et al. (2001) Proc Natl Acad Sci USA 98(8) 4552-4557. Thus, one skilled in the art could generate a large number of nucleotide and/or polypeptide variants having, for example, at least 95-99% identity to the reference sequence described herein and screen such for desired phenotypes according to methods routine in the art.

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity=X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by Ile, Leu by Ile, and Ser by Thr. Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

"Highly stringent hybridization conditions" are defined as hybridization at 65° C. in a 6×SSC buffer (i.e., 0.9 M sodium chloride and 0.09 M sodium citrate). Given these conditions, a determination can be made as to whether a given set of sequences will hybridize by calculating the melting temperature ($T_m$) of a DNA duplex between the two sequences. If a particular duplex has a melting temperature lower than 65° C. in the salt conditions of a 6×SSC, then the two sequences will not hybridize. On the other hand, if the melting temperature is above 65° C. in the same salt conditions, then the sequences will hybridize. In general, the melting temperature for any hybridized DNA:DNA sequence can be determined using the following formula: $T_m$, =81.5° C.+16.6($\log_{10}$[Na$^+$])+0.41(fraction G/C content)−0.63(% formamide)−(600/l). Furthermore, the $T_m$, of a DNA:DNA hybrid is decreased by 1-1.5° C. for every 1% decrease in nucleotide identity (see e.g., Sambrook and Russel, 2006).

Host cells can be transformed using a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754). Such techniques include, but are not limited to, viral infection, calcium phosphate transfection, liposome-mediated transfection, microprojectile-mediated delivery, receptor-mediated uptake, cell fusion, electroporation, and the like. The transfected cells can be selected and propagated to provide recombinant host cells that comprise the expression vector stably integrated in the host cell genome.

Exemplary nucleic acids which may be introduced to a host cell include, for example, DNA sequences or genes from another species, or even genes or sequences which originate with or are present in the same species, but are incorporated into recipient cells by genetic engineering methods. The term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the cell, DNA from another individual of the same type of organism, DNA from a different organism, or a DNA generated externally, such as a DNA sequence containing an antisense message of a gene, or a DNA sequence encoding a synthetic or modified version of a gene.

Host strains developed according to the approaches described herein can be evaluated by a number of means known in the art (see e.g., Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Methods of down-regulation or silencing genes are known in the art. For example, expressed protein activity can be down-regulated or eliminated using antisense oligonucleotides, protein aptamers, nucleotide aptamers, and RNA interference (RNAi) (e.g., small interfering RNAs (sRNA), short hairpin RNA (shRNA), and micro RNAs (miRNA) (see e.g., Fanning and Symonds (2006) Handb Exp Pharmacol. 173, 289-303G, describing hammerhead ribozymes and small hairpin RNA; Helene, C., et al. (1992) Ann. N.Y.

Acad. Sci. 660, 27-36; Maher (1992) Bioassays 14(12): 807-15, describing targeting deoxyribonucleotide sequences; Lee et al. (2006) Curr Opin Chem Biol. 10, 1-8, describing aptamers; Reynolds et al. (2004) Nature Biotechnology 22(3), 326-330, describing RNAi; Pushparaj and Melendez (2006) Clinical and Experimental Pharmacology and Physiology 33(5-6), 504-510, describing RNAi; Dillon et al. (2005) Annual Review of Physiology 67, 147-173, describing RNAi; Dykxhoorn and Lieberman (2005) Annual Review of Medicine 56, 401-423, describing RNAi). RNAi molecules are commercially available from a variety of sources (e.g., Ambion, TX; Sigma Aldrich, MO; Invitrogen). Several siRNA molecule design programs using a variety of algorithms are known to the art (see e.g., Cenix algorithm, Ambion; BLOCK-iT™ RNAi Designer, Invitrogen; siRNA Whitehead Institute Design Tools, Bioinformatics & Research Computing). Traits influential in defining optimal siRNA sequences include G/C content at the termini of the siRNAs, Tm of specific internal domains of the siRNA, siRNA length, position of the target sequence within the CDS (coding region), and nucleotide content of the 3' overhangs.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

Formulation can be conducted as described in U.S. Pat. No. 8,318,156, issued 27 Nov. 2012, and incorporated herein by reference in its entirety.

Formulation can include compounds disclosed in US App Pub. No. 2011/0142816, published on 16 Jun. 2011, and incorporated herein by reference in its entirety.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations can be formulated to extend the activity of the mutant CocE polypeptide and reduce dosage frequency. Controlled-release preparations can also be used to effect the time of onset of action or other characteristics, such as blood levels of the agent, and consequently affect the occurrence of side effects. Controlled-release preparations can be designed to initially release an amount of mutant CocE polypeptide that produces the desired therapeutic effect, and gradually and continually release other amounts to maintain the level of therapeutic effect over an extended period of time. In order to maintain a near-constant level of mutant CocE polypeptide in the body, the agent can be released from the dosage form at a rate that will replace the amount of agent being metabolized and/or excreted from the body. The controlled-release of an agent can be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

Therapeutic Methods

Another aspect of the invention is directed toward a catalytic degradation approach to anti-cocaine therapeutics. Provided are treatments, both prophylactic and therapeutic, of cocaine-induced conditions through the administration of mutant CocE polypeptides described herein to a subject in need thereof. The cocaine esterase variants of the invention hold significant clinical value because of their properties described herein, which include increased thermostability or longer plasma half-life than known naturally occurring CocE. It is this increase in thermostability and plasma half-life that can provide a much more rapid response to the life-threatening symptoms of cocaine toxicity that sets the CocE variants of the present disclosure apart from other treatment options.

Therapeutic methods can be as described in U.S. Pat. No. 8,318,156, issued 27 Nov. 2012, and incorporated herein by reference in its entirety.

Methods described herein are generally performed on a subject in need thereof. A cocaine-induced condition can include, but is not limited to, cocaine overdose, cocaine toxicity, and cocaine dependence and/or addiction. For example, the diagnosis of cocaine toxicity can include convulsions, grand-mal seizures, cardiac arrest, myocardial infarction, cardiac arrhythmias, increased blood pressure, stroke, drug-induced psychosis, dissecting aneurysm, and increased myocardial oxygen demand. As another example, in the case of cocaine dependence or addiction, withdrawal symptoms can include subjective sensations of mild to severe dysphora, depression, anxiety, or irritability.

A subject in need of the therapeutic methods described herein can be a subject having, diagnosed with, suspected of having, or at risk for developing a cocaine-induced condition. Subjects with an identified need of therapy include those with a diagnosed cocaine-induced condition, an indication of a cocaine-induced condition, and subjects who have been treated, are being treated, or will be treated for a cocaine-induced condition. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, hamsters, guinea pigs, and chickens, and humans. For example, the subject can be a human subject.

An effective amount of the mutant CocE polypeptides described herein is generally that which can reduce the cocaine-toxicity or the severity of a cocaine-induced condition. Reduction in severity includes, for example, an arrest or a decrease in symptoms, physiological indicators, biochemical markers, or metabolic indicators. When used in the methods of the invention, a therapeutically effective amount of mutant CocE polypeptide described herein can be employed in pure form or, where such forms exist, in pharmaceutically acceptable salt form and with or without a pharmaceutically acceptable excipient. For example, the mutant CocE polypeptides of the invention can be administered at a reasonable benefit/risk ratio applicable to any medical treatment, in an amount sufficient to substantially reduce the cocaine concentration in the blood or tissues of the subject.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

When used in the treatments described herein, a therapeutically effective amount of a mutant CocE described herein can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially reduce the cocaine concentration in the blood and/or tissues of the subject.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses. Agent administration can occur as a single event or over a time course of treatment. For example, an agent can be administered daily, weekly, bi-weekly, or monthly. For some conditions, treatment could extend from several weeks to several months or even a year or more.

Mutant CocE polypeptides described herein can also be used in combination with other therapeutic modalities. Thus, in addition to the therapies described herein, one can also provide to the subject other therapies known to be efficacious for particular cocaine-induced conditions.

A mutant CocE polypeptide can be administered simultaneously or sequentially with another agent, such as an antibiotic, an antiinflammatory, or another agent. For example, a mutant CocE polypeptide can be administered simultaneously with another agent, such as an antibiotic or an antiinflammatory. Simultaneous administration can occur through administration of separate compositions, each containing one or more of a mutant CocE polypeptide, an antibiotic, an antiinflammatory, or another agent. Simultaneous administration can occur through administration of one composition containing two or more of a mutant CocE polypeptide, an antibiotic, an antiinflammatory, or another agent. A mutant CocE polypeptide can be administered sequentially with an antibiotic, an antiinflammatory, or another agent. For example, a mutant CocE polypeptide can be administered before or after administration of an antibiotic, an antiinflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

Administration can be as described in U.S. Pat. No. 8,318,156, issued 27 Nov. 2012, and incorporated herein by reference in its entirety.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 μm), nanospheres (e.g., less than 1 μm), microspheres (e.g., 1-100 μm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Pulmonary delivery of macromolecules, such as mutant CocE polypeptides, can provide relatively easy, non-invasive administration to the circulatory system for systemic distribution (see e.g., Cryan (2004) AAPS J. 7(1) article 4, E20-41, providing a review of pulmonary delivery technology). Advantages of pulmonary delivery include noninvasiveness, large surface area for absorption (~75 $m^2$), thin (~0.1 to 0.5 μm) alveolar epithelium permitting rapid absorption, absence of first pass metabolism, decreased proteolytic activity, rapid onset of action, and high bioavailablity. Various inhalation delivery devices, such as metered-dose inhalers, nebulizers, and dry-powder inhalers, that can be used to deliver the biomolecules described herein are known to the art (e.g., AErx (Aradigm, CA); Respimat (Boehringer, Germany); AeroDose (Aerogen Inc., CA)). Dry powder inhalation devices are particularly preferred for pulmonary delivery of protein-based agents (e.g., Spinhaler (Fisons Pharmaceuticals, NY); Rotohaler (GSK, NC); Diskhaler (GSK, NC); Spiros (Dura Pharmaceuticals, CA); Nektar (Nektar Pharmaceuticals, CA)).

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Examples of carrier delivery systems for with mutant CocE polypeptides described herein include microspheres (see e.g., Varde & Pack (2004) Expert Opin. Biol. 4(1) 35-51), hydrogels (see generally, Sakiyama et al. (2001) FASEB J. 15, 1300-1302), polymeric implants (see generally, Teng et al (2002) Proc. Natl. Acad. Sci. U.S.A. 99, 3024-3029), smart ploymeric carriers (see generally, Stayton et al. (2005) Orthod Craniofacial Res 8, 219-225; Wu et al. (2005) Nature Biotech (2005) 23(9), 1137-1146), and liposomes (see e.g., Galovic et al. (2002) Eur. J. Pharm. Sci. 15, 441-448; Wagner et al. (2002) J. Liposome Res. 12, 259-270). In some embodiments, the mutant CocE polypeptide can be encapsulated in a red blood cell.

Screening

Also provided are methods for screening.

Another aspect of the invention is directed toward screening methods for the generation, identification, and purification of mutant CocE polypeptides. Generally, mutant CocE polypeptides can be initially designed according to the approaches described above. Such designed polypeptides can then be screened for preferred characteristics, such as retention of hydrolytic efficiency, increased thermostability, increased plasma-half-life, or reduced antigenicity. Also, random mutant CocE polypeptides can be screened for the desired characteristics.

Detection methods to screen for mutants encompass a wide variety of techniques. The following is an exemplary summary of a generic protocol. Nucleic acid encoding the mutant CocE polypeptides (generated, for example, through rational design, random mutagenesis, or host mutagensis) is transformed into an appropriate expression host (for example, *E. coli* cells such as *E. coli* BL21 Gold (Stratagene)), and expression of the mutant polypeptide is induced according to standard protocols (e.g. by IPTG). Expression is performed at temperatures to produce optimal protein expression (e.g., 16° C. for CocE) for a pre-determined period of time (e.g., anywhere from 30 minutes to 24 hours or longer). Alternatively, expression is performed at an elevated temperature (for example, the elevated temperature can be at least about 35° C., at least about 36° C., at least about 37° C., at least about 38° C., at least about 39° C., at least about 40° C., or even higher). Preferably, the elevated temperature at which mutated CocE polypeptide is expressed is 37° C. Around this temperature, wild-type CocE polypeptide partitions almost exclusively into inclusion bodies. Cells containing the expressed mutant polypeptides are screened for the presence of thermostable variants of CocE.

Screening for the presence of thermostable variants of CocE generally involves either direct measurement on cultured cells, on cell lysates, or following cellular disruption and isolation of the mutant CocE polypeptide. Cellular disruption can include osmotic shock, chemical lysis, sonication, and/or homogenization, and isolation of the mutant polypeptide can be obtained through numerous methods including either direct absorption to a matrix or affinity absorption through the use of anti-cocaine antibodies or fusion-protein specific capture systems. Suitable matrix for absorption includes nitrocellulose paper, filters, untreated or affinity-treated microtiter plates, agarose or sepharose resins, and/or affinity-coated tips.

The esterase activity of the cultured cells or isolated mutant polypeptide can be subsequently measured at one or more temperatures to determine the thermostability of the mutants. The temperature at which the activity assay is performed determines the degree of thermostability detection. Thus, while the final mutants will preferably have a melting temperature of 45° C. or higher (as determined by, for example, circular dichroism), often, the initial screening at 45° C. will not find active enzymes. Rather, several cycles of mutagenesis and screening at subsequently increasing temperatures can be performed to achieve thermostable mutants. Thus, initial screening can be performed at 30° C., and after further cycles of mutagenesis, screening can be performed with incrementally increasing temperatures (for example, 34° C., 37° C., 40° C., 42.5° C., 45° C., etc.), until a mutant of suitable thermostability is achieved. The incremental temperature increases are determined empirically during the procedure, and are affected by the number of hits at particular temperatures and the determined Tm of the generated mutants.

Screening can be conducted as described in U.S. Pat. No. 8,318,156, issued 27 Nov. 2012, and incorporated herein by reference in its entirety.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a mutant CocE polypeptide. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: CocE Sequence

The following example shows the sequence listing for bacterial CocE (Gene cloning and nucleotide sequencing and properties of a cocaine esterase from *Rhodococcus* sp. strain MB1. Bresler M. M., Rosser S. J., Basran A., Bruce N. C. Appl. Environ. Microbiol. 66:904-908(2000)). Cysteine positions 107, 429, 477, and 551 are underlined below in SEQ ID NO: 1.

```
>sp|Q9L9D7|COCE_RHOSM Cocaine esterase
OS = Rhodococcus sp. (strain MB1 Bresler)
GN = cocE PE = 1 SV = 1:
                                            SEQ ID NO: 1
MVDGNYSVASNVMVPMRDGVRLAVDLYRPDADGPVPVLLVRNPYDKF

DVFAWSTQSTNWLEFVRDGYAVVIQDTRGLFASEGEFVPHVDDEADA

EDTLSWILEQAWCDGNVGMFGVSYLGVTQWQAAVSGVGGLKAIAPSM

ASADLYRAPWYGPGGALSVEALLGWSALIGTGLITSRSDARPEDAAD

FVQLAAILNDVAGAASVTPLAEQPLLGRLIPWVIDQVVDHPDNDESW

QSISLFERLGGLATPALITAGWYDGFVGESLRTFVAVKDNADARLVV
```

-continued
```
GPWSHSNLTGRNADRKFGIAATYPIQEATTMHKAFFDRHLRGETDAL

AGVPKVRLFVMGIDEWRDETDWPLPDTAYTPFYLGGSGAANTSTGGG

TLSTSISGTESADTYLYDPADPVPSLGGTLLFHNGDNGPADQRPIHD

RDDVLCYSTEVLTDPVEVTGTVSARLFVSSSAVDTDFTAKLVDVFPD

GRAIALCDGIVRMRYRETLVNPTLIEAGEIYEVAIDMLATSNVFLPG

HRIMVQVSSSNFPKYDRNSNTGGVIAREQLEEMCTAVNRIHRGPEHP

SHIVLPIIKR
```

Example 2: CocE MUTANTS

The following example describes amino acid replacements in CocE and activity thereof. The following cysteine-mutated CocE mutants were fully sequenced and the activity tested (see e.g., FIG. 3A-E):

| NAME | SUBSTITUTIONS |
|---|---|
| Lys 2: | C107S, C429S; |
| Ala328: | C107S, C429S, A328C; |
| Asp18: | D18C, C107S, C429S; |
| Thr12: | C107S, C429S, T436C; and |
| Val434: | C107S, C429S, V434C. |

Activity was also tested for the following CocE mutants: L163V; V121 D; S167A; S167A/W52L; Q123E; S159A; T122A; S140A; T172R; S265A; W220A; A193D; and Y532F.

S167A mutant results did not show enhanced activity compared to wild-type. S159A mutant showed some degree of thermostability. T122A showed some degree of thermostability. T172R mutant showed enhanced activity compared to WT.

The following mutations were also envisioned as amino acid replacements: S265A; W220A; A193D; and Y532F.

Example 3: Generation of Mutants

Figure 4:
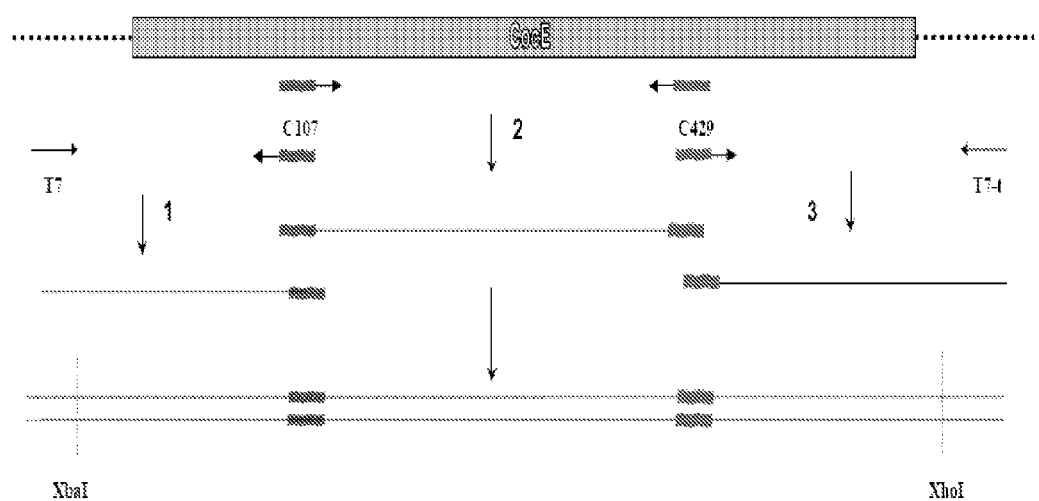
FIG. 4 is a drawing depicting the removal of Cys 107 and Cys 429.
Figure 5:
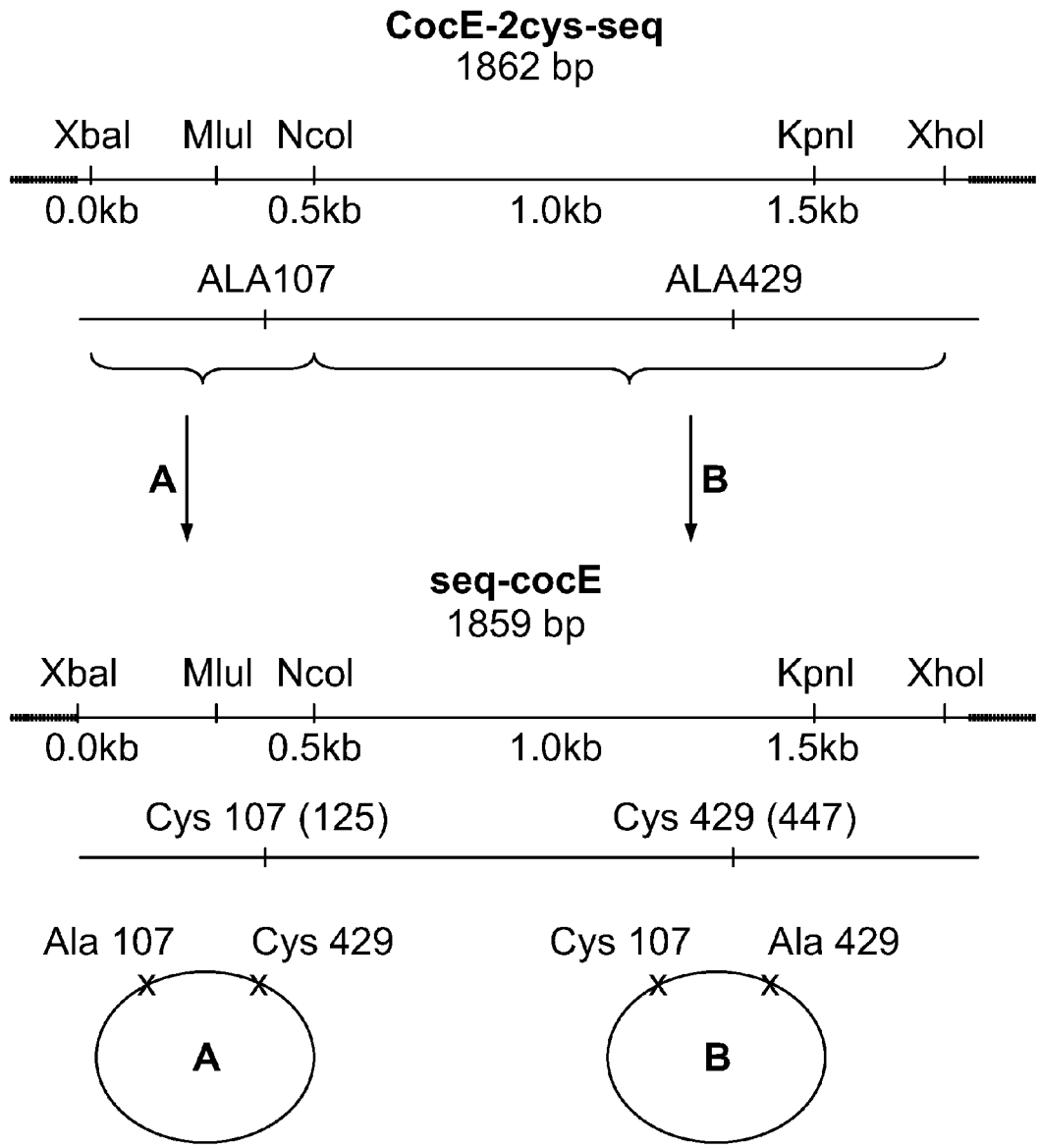
FIG. 5 is a drawing depicting the removal of Cys 107 and replacing with Ala and leaving Cys 429 as is in one CocE and removal of Cys429 and replacing with Ala and leaving the Cys 107 as is.
Figure 6:
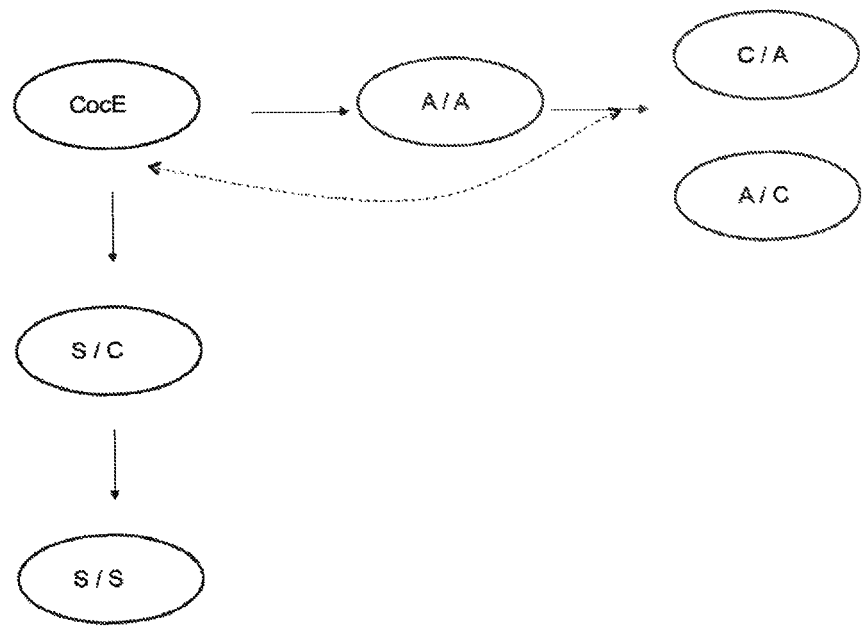
FIG. 6 is a cartoon depicting strategy for study of additional mutations.

The following example describes various mutants. Double 107/429 mutants were generated by primer extension, replacing Cys with Ala (see e.g., FIG. 4). Additional mutations were further studied and tested for activity (see e.g., FIG. 5 and FIG. 6). Results are shown in TABLE 1.

TABLE 1

CocE Mutants and Cocaine Esterase Activity

| Mutant Name | Substitutions | Cocaine Esterase Activity relative to WT |
|---|---|---|
| 2 Ala#2 | C107A/C429A | None |
| A5 | C107A | Low |
| B8 | C429A | Lower |
| RetWT-6 | C107C/C429S | Ok |
| 1 Ser-3(107) | C107S | Ok |
| 2 Ser#2 | C107S/C429S | Ok |
| Lys#2 | C107S/C429S/K315C | None |
| Thr#12 | C107S/C429S/T429C | None |
| Asp#4 | C107S/C429S/D18C | None |
| Val434 #6 | C107S/C429S/V434C | Tbd |
| Ala328 #2 | C107S/C429S/A328C | Tbd |

The invention claimed is:

1. A composition comprising an isolated mutant cocaine esterase (CocE) polypeptide comprising:
an amino acid sequence having at least about 95% sequence identity to SEQ ID NO: 1 having-two or more substitutions at an amino acid position selected from the group consisting of C107, C429, and C551;
wherein the polypeptide has cocaine esterase activity.

2. The composition of claim 1, wherein the-two or more substitutions are selected from the group consisting of C107S, C429S, and C551S.

3. The composition of claim 2, wherein the-two or more substitutions comprise C107S and C429S.

4. The composition of claim 1, wherein the-two or more substitutions are not C107A, C429A, or C551A.

5. The composition of claim 1, wherein the CocE polypeptide further comprises one or more of a substitution, addition, or deletion selected from the group consisting of A328C, D18C, T436C, V434C, L163V; V121D; S167A, W52L, Q123E, S159A, T122A, S140A, T172R, G173Q, S265A, W220A, A193D, and Y532F.

6. The composition of claim 1, wherein the CocE polypeptide further comprises one or more substitutions selected from the group consisting of: R41I; N42V; Y44F; D45R; F47R; K46A; S56G; T74S; F84Y; S117A; L119A; G173Q; S140A; L146P; A149S; Y152H; S159A; V160A; L163V; L169K; G171A; T172R; G173A; L174R; S177Q; A181K; S179R; R182K; F189A; F189K; F189L; V190K; Q191K; A193D; A194K; A194R; N197K; I218L; W220A; V225I; T254R; V262L; S265A; W285T; A310D; C477T; L508G; K531A; Y532F; D533S; T172R/G173Q; T172R/A193D; T172R/F189K; T172R/G173Q-I175-G-G-A186; G171Q/T172R/G173Q, T172R/G173Q-T176-G-G-D185; G173Q-I175-G-G-A186; G173Q-T176-G-G-D185; I175-G-G-A186; T176-G-G-D185; wt-I175-G-G-D185; wt-T176-G-G-D185; F189A/T172R; R75K; F78C; F78R; A79K; A79R; Y118S; V121Y; L164K; W166R; I170V; G173Q; T176R; S177C; K315C; G171S; D180K; P183K; F78C/S177C; and Y118S/V121Y.

7. The composition of claim 1, wherein the CocE polypeptide further comprises one or more substitutions selected from the group consisting of: R41I; N42V; Y44F; D45R; F47R; K46A; S56G; T74S; F84Y; S117A; L119A; G173Q; S140A; L146P; A149S; Y152H; S159A; V160A; L163V; L169K; G171A; T172R; G173A; L174R; S177Q; A181K; S179R; R182K; F189A; F189K; F189L; V190K; Q191K; A193D; A194K; A194R; N197K; I218L; W220A; V225I; T254R; V262L; S265A; W285T; A310D; C477T; L508G; K531A; Y532F; D533S; T172R/G173Q; T172R/A193D; T172R/F189K; T172R/G173Q-I175-G-G-A186; G171Q/T172R/G173Q, T172R/G173Q-T176-G-G-D185; G173Q-I175-G-G-A186; G173Q-T176-G-G-D185; I175-G-G-A186; T176-G-G-D185; wt-I175-G-G-D185; wt-T176-G-G-D185; and F189A/T172R.

8. The composition of claim 1, wherein the CocE polypeptide further comprises one or more substitutions selected from the group consisting of: R75K; F78C; F78R; A79K; A79R; Y118S; V121Y; L164K; W166R; I170V; G173Q; T176R; S177C; K315C; G171S; D180K; P183K; F78C/S177C; and Y118S/V121Y.

9. The composition of claim 1, further comprising:
a polymeric molecule,
wherein the polymeric molecule is chemically linked to one or more amino acid residues the mutant CocE polypeptide.

10. The composition of claim 9, wherein
at least one of C107, C429, C551, and C477 is not substituted; and
the polymeric molecule is chemically linked to the mutant CocE polypeptide at the non-substituted amino acid position selected from C107, C429, C551, and C477.

11. The composition of claim 9, wherein the polymeric molecule is chemically linked to a substituted or added amino acid residue of the mutant CocE polypeptide.

12. The composition of claim 9, wherein the polymeric molecule comprises a molecular weight of about 300 Daltons up to about 20,000 Daltons.

13. The composition of claim 9, wherein the polymeric molecule comprises a molecular weight of about 300 Daltons, about 500 Daltons, about 750 Daltons, about 1000 Daltons, about 1500 Daltons, about 2000 Daltons, about 2500 Daltons, about 3000 Daltons, about 3500 Daltons, about 4000 Daltons, about 4500 Daltons, about 5000 Daltons, about 5500 Daltons, about 6000 Daltons, about 6500 Daltons, about 7000 Daltons, about 7500 Daltons, about 8000 Daltons, about 8500 Daltons, about 9000 Daltons, about 9500 Daltons, about 10000 Daltons, about 10500 Daltons, about 11000 Daltons, about 11500 Daltons, about 12000 Daltons, about 12500 Daltons, about 13000 Daltons, about 13500 Daltons, about 14000 Daltons, about 14500 Daltons, about 15000 Daltons, about 15500 Daltons, about 16000 Daltons, about 16500 Daltons, about 17000 Daltons, about 17500 Daltons, about 18000 Daltons, about 18500 Daltons, about 19000 Daltons, about 19500 Daltons, or about 20000 Daltons.

14. The composition of claim 9, wherein the polymeric molecule comprises a polyethylene glycol (PEG).

15. The composition of claim 9, wherein the polymeric molecule is selected from the group consisting of 2-[2-(Boc-amino)ethoxy]ethoxyacetic acid (dicyclohexylammonium); 21-(Boc-amino)-4,7,10,13,16,19-hexaoxaheneicosanoic acid purum; 15-(Boc-amino)-4,7,10,13-tetraoxapentadecanoic acid purum; N-Boc-2,2'-(ethylenedioxy)diethylamine; N-Boc-N'-succinyl-4,7,10-trioxa-1,13-tridecanediamine; 2-[2-(Fmoc-amino)ethoxy]ethanol; N-Fmoc-N''-succinyl-4,7,10-trioxa-1,13-tridecanediamine; 4,7,10,13,16,19,22,25,32,35,38,41,44,47,50,53-Hexadecaoxa-28,29-dithiahexapentacontanedioic acid; 4,7,10,13,16,19,22,25,32,35,38,41,44,47,50,53-Hexadecaoxa-28,29-dithiahexapentacontanedioic acid di-N-succinimidyl ester; O,O'-Bis(2-aminoethyl)octadecaethylene glycol; {2-[2-(Fmoc-amino)ethoxy]ethoxy}acetic acid; 2-[2-(2-Methoxyethoxy)ethoxy]acetic acid; methoxypolyethylene glycol maleimide; O-(2-Azidoethyl)-O'-methyl-triethylene glycol; O-(2-Azidoethyl)-O'-methyl-undecaethylene glycol; O-(2-Azidoethyl)nonadecaethylene glycol; O,O'-Bis[2-(N-Succinimidyl-succinylamino)ethyl]polyethylene glycol; O,O'-Bis[2-(N-Succinimidyl-succinylamino)ethyl]polyethylene glycol; O-(3-Carboxypropyl)-O'-[2-(3-mercaptopropionylamino)ethyl]-polyethylene glycol; O—[N-(3-Maleimidopropionyl)aminoethyl]-O'-[3-(N-succinimidyloxy)-3-oxopropyl]triethylene glycol; Methoxypolyethylene glycol azide PEG; Methoxypolyethylene glycol; and O-[2-(3-Tritylthiopropionylamino)ethyl]polyethylene glycol.

16. The composition of claim 1, wherein the mutant CocE polypeptide has at least about 60%, at least about 65%, at least about 70%, at least about 75%, at least about 80%, at least about 85%, at least about 90%, at least about 95%, at least about 100%, at least about 105%, at least about 110%, at least about 115%, at least about 120%, at least about 125%, at least about 130%, at least about 135%, or at least about 140% of the esterase activity of a wild-type CocE polypeptide.

17. The composition of claim 1, wherein the mutant CocE polypeptide is at least about 2.1 kcal/mol, at least about 2.2 kcal/mol, at least about 2.3 kcal/mol, at least about 2.4 kcal/mol, at least about 2.5 kcal/mol, at least about 2.6 kcal/mol, at least about 2.7 kcal/mol, at least about 2.8 kcal/mol, at least about 2.9 kcal/mol, at least about 3.0 kcal/mol, at least about 3.1 kcal/mol, at least about 3.2 kcal/mol, at least about 3.3 kcal/mol, at least about 3.4 kcal/mol, at least about 3.5 kcal/mol, at least about 3.6 kcal/mol, at least about 3.7 kcal/mol, at least about 3.8 kcal/mol, at least about 3.9 kcal/mol, at least about 4.0 kcal/mol, at least about 4.1 kcal/mol, at least about 4.2 kcal/mol, at least about 4.3 kcal/mol, at least about 4.4 kcal/mol, or at least about 4.5 kcal/mol more thermostable as compared to wild-type CocE.

18. The composition of claim 1, having reduced immunogenicity as compared to a composition comprising a wild-type CocE.

19. The composition of claim 1, wherein the mutant CocE polypeptide retains at least substantially the same or greater catalytic efficiency of wild-type CocE polypeptide.

20. A pharmaceutical composition comprising the composition of claim 1 and a pharmaceutically acceptable carrier or excipient.

21. An isolated nucleic acid encoding the mutant CocE polypeptide of the composition of claim 1.

22. A method of treating a cocaine-induced condition comprising administering to a subject in need thereof an effective amount of the composition of claim 1 or a composition comprising the isolated nucleic acid of claim 21.

23. The method of claim 22, wherein the cocaine-induced condition is selected from the group consisting of cocaine overdose, cocaine toxicity, cocaine addiction, and cocaine dependence.

* * * * *